(12) United States Patent
Azerad et al.

(10) Patent No.: US 7,241,601 B2
(45) Date of Patent: Jul. 10, 2007

(54) PROCESS FOR THE PREPARATION OF FEXOFENADINE

(75) Inventors: Robert Azerad, Ris Orangis (FR); Jacques Biton, La Croix Saint Ouen (FR); Isabelle Lacroix, Choisy le Roi (FR)

(73) Assignee: Aventis Pharma SA, Paris (FR)

( * ) Notice: Subject to any disclaimer, the term of this patent is extended or adjusted under 35 U.S.C. 154(b) by 431 days.

(21) Appl. No.: 10/392,699

(22) Filed: Mar. 20, 2003

(65) Prior Publication Data

US 2006/0019358 A1    Jan. 26, 2006

Related U.S. Application Data

(62) Division of application No. 09/646,517, filed as application No. PCT/FR99/00625 on Mar. 18, 1999, now Pat. No. 6,558,931.

(30) Foreign Application Priority Data

Mar. 19, 1998 (FR) ................................... 98 03349

(51) Int. Cl.
*C12P 17/12* (2006.01)
*C12N 1/20* (2006.01)
(52) U.S. Cl. .................................... 435/122; 435/253.5
(58) Field of Classification Search ................ 435/122, 435/253.5
See application file for complete search history.

(56) References Cited

U.S. PATENT DOCUMENTS

| | | | |
|---|---|---|---|
| 5,990,127 A * | 11/1999 | Meiwes et al. ............. | 514/317 |
| 6,147,216 A | 11/2000 | Krauss et al. | |
| 6,242,606 B1 | 6/2001 | Krauss et al. | |
| 6,340,761 B1 | 1/2002 | Krauss et al. | |
| 6,348,597 B2 | 2/2002 | Krauss et al. | |
| 6,441,179 B1 | 8/2002 | Krauss et al. | |
| 6,479,663 B2 | 11/2002 | Krauss et al. | |
| 6,548,675 B2 | 4/2003 | Krauss et al. | |
| 6,552,200 B2 | 4/2003 | Krauss et al. | |
| 6,555,689 B2 | 4/2003 | Krauss et al. | |
| 6,558,931 B1 * | 5/2003 | Azerad et al. ............. | 435/122 |
| 6,559,312 B2 | 5/2003 | Krauss et al. | |
| 6,566,526 B2 | 5/2003 | Krauss et al. | |
| 6,777,555 B2 | 8/2004 | Krauss et al. | |

OTHER PUBLICATIONS

U.S. Appl. No. 08/082,693, filed Jun. 25, 1993, Krauss, et al.
U.S. Appl. No. 08/144,084, filed Oct. 27, 1993, Krauss, et al.
U.S. Appl. No. 08/237,466, filed May 11, 1994, Krauss, et al.
Chan, et al., Direct enantiomeric separation of terfenadine and its major acid metabolite by high-performance liquid chromatography, and the lack of steroselective tefenadine enantiomer biotransformation in man, Journal of Chromatography: Biomedical Applications, vol. 571 (1991), pp. 291-297.
Absidia corymbifera Web Site: www.doctorfungus.org/thefungi/absidia.htm Aug. 21, 2002

* cited by examiner

*Primary Examiner*—Herbert J. Lilling
(74) *Attorney, Agent, or Firm*—Jiang Lin

(57) ABSTRACT

A process for the preparation of a compound of the formula (I)

Figure 1:
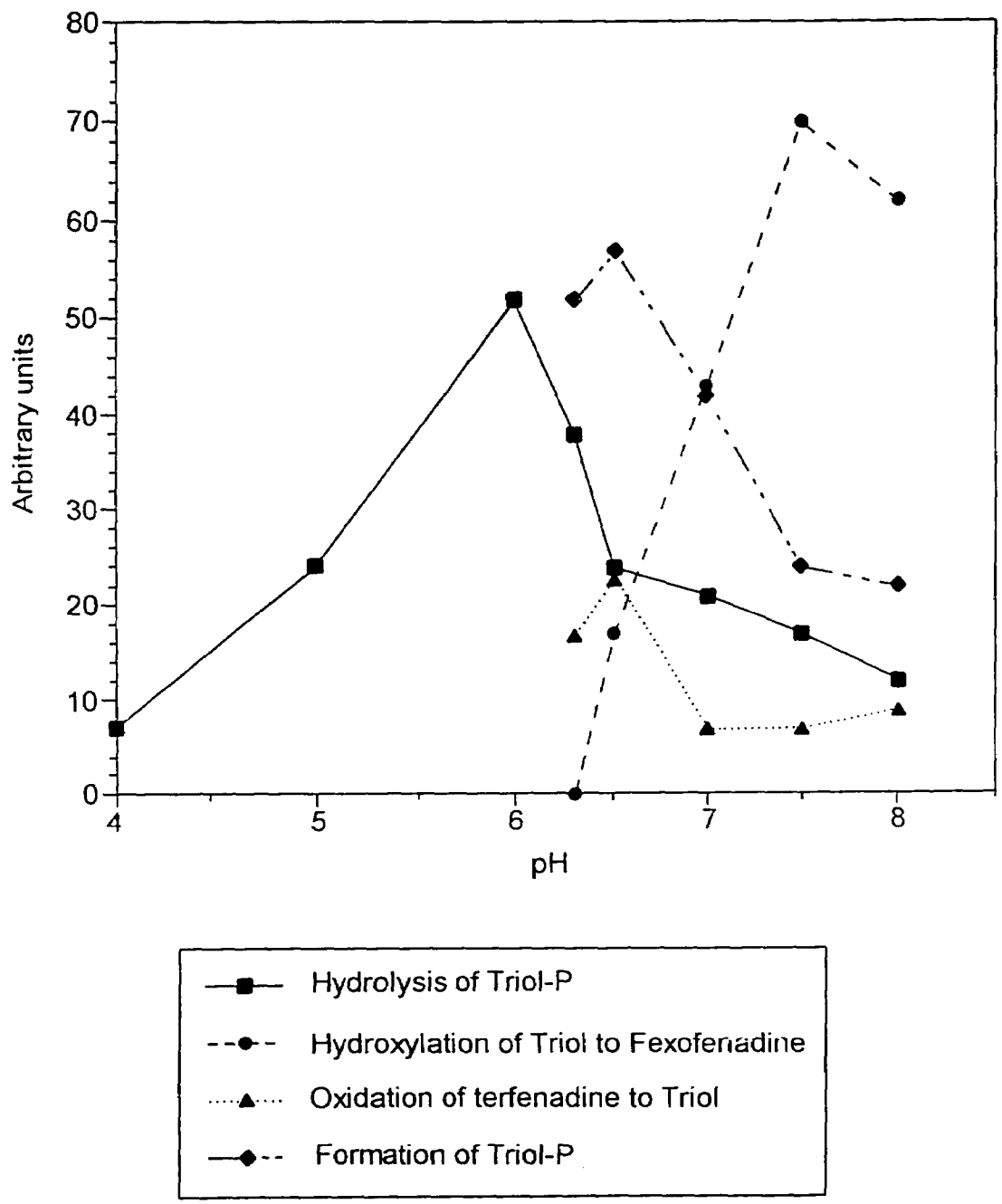

by means of bioconversion with a microorganism culture of a compound of the formula

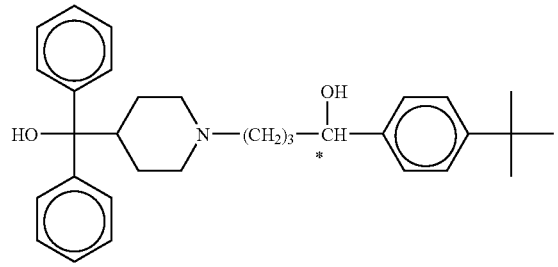

(II)

6 Claims, 4 Drawing Sheets

PROCESS FOR THE PREPARATION OF FEXOFENADINE

This application is a division of U.S. patent application Ser. No. 09/646,517 filed Oct. 31, 2000, now U.S. Pat. No. 6,558,931, which is a 371 of PCT/FR99/00625 filed Mar. 18, 1999.

A subject of the present invention is a new process for the preparation of Fexofenadine.

Fexofenadine is a medicament which has a significant antihistaminic activity and which is free from side effects. (Efficacy and safety of Fexofenadine hydrochloride for treatment of seasonal allergic rhinitis, Bernstein D. I. et al, Ann. Allergy-Asthma-Immunol. (1997) 79(5) 443–448).

This compound is the principal metabolite of Terfenadine, itself an antihistaminic agent (D. Mc Tavish, K L Goa and M. Ferill, "terfenadine: an updated review of its pharmacological properties and therapeutic efficiency, Drug 39, 552–574 (1989)).

Fexofenadine is currently prepared by chemical route, in numerous stages with a yield of less than 10% (U.S. Pat. Nos. 5,578,610 and 5,581,011).

The Applicant therefore proposes to find another synthesis route for Fexofenadine. The choice is then concentrated on a bioconversion method using one of the following very specific two types of microorganisms: either the filamentous fungi of the *Absidia Corymbifera* genus and in particular *Absidia Corymbifera* LCP 63-1800, or a *Streptomyces* and in particular *Streptomyces platensis* NRRL 2364.

The specificity of the bioconversion with these microorganisms was unexpected: among the numerous strains studied during a screening, these are the only ones which allow Fexofenadine to be obtained with a good yield and little or no by-products.

A subject of the invention is a process for the preparation of the compounds of formula (I):

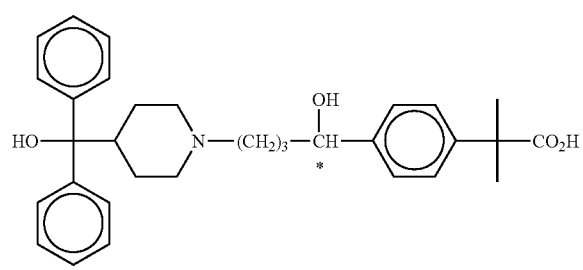

(I)

characterized in that a bioconversion of the compound or compounds of formula (II) is carried out:

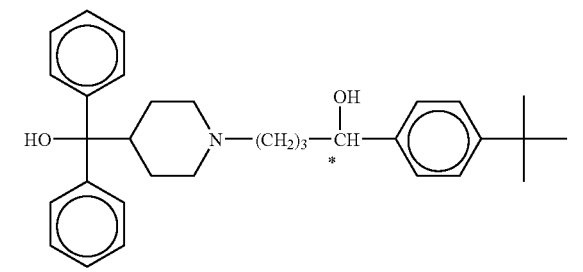

(II)

with either a microorganism culture of the *Absidia corymbifera* genus or a microorganism culture of the *Streptomyces* genus, at a pH comprised between 5.0 and 8.0, in order to obtain the expected compound or compounds of formula (I), which if appropriate are isolated, purified and/or salified, the compounds of formulae (I) or (II) being able to be in the two possible enantiomeric forms, isolated or in mixtures.

The asterisk indicates the position of the asymmetrical carbon.

A particular subject of the invention is a preparation process as described above in which the *Absidia corymbifera* is *Absidia corymbifera* LCP 63–1800 or in which the *Streptomyces* is *Streptomyces platensis* NRRL 2364.

Fexofenadine is a racemic mixture of the enantiomers of formula (I). A more particular subject of the process is therefore the process as described previously in which a bioconversion of Terfenadine, corresponding to a racemic mixture of the two enantiomers of formula (II), is carried out in order to obtain Fexofenadine, corresponding to a racemic mixture of the enantiomers of formula (I).

*Absidia corymbifera* and in particular *Absidia corymbifera* LCP 63-1800 are available from the Laboratoire de Cryptogamie du Muséum d'Histoire Naturelle de Paris [The Cryptogam Laboratory at the Paris Natural History Museum].

Among the *Streptomyces* which can be used in the process, which is a subject of this Application, the following *Streptomyces* can be mentioned:

Streptomyces albus
Streptomyces ambofaciens ATCC 15154
Streptomyces antibioticus ATCC 31771
Streptomyces aureofaciens ATCC 10762
Streptomyces djakartensis
Streptomyces erythraeus
Streptomyces felleus DSM 40130
Streptomyces fradiae W3554
Streptomyces griseus NRRL B150
Streptomyces JSP-2 (FH2126)
Streptomyces lividans JT46/pCS2
Streptomyces narbonensis FH 2102
Streptomyces olivaceus ATCC 3335
Streptomyces platensis ATCC 13865
Streptomyces platensis NRRL 2364
Streptomyces rimosus 2234
Streptomyces venezuelae NRRL B-2446.

It is known to a person skilled in the art that the extreme simplicity of bacterial cells, without a distinct nucleus, allows them to be classified as prokaryotes. This is the case for *Streptomyces*, filamentous bacteria, which are aerobes and gram-positive. On the other hand, the other microorganisms are called eukaryotes such as, for example, the filamentous fungi and quite particularly *Absidia corymbifera*. Their cells are differentiated in particular from the prokaryotes by the presence of a nucleus and numerous cytoplasmic organelles.

The process described above, which is a subject of the present Application, offers numerous advantages. On the one hand, it avoids the chemical route which requires numerous synthesis stages accompanied by necessary isolation processes at each of these reaction stages. In the case of an industrial use, this route can prove to be expensive and polluting.

In the case of the process which is a subject of this Application, a single operation is necessary and the optional purification stage essentially only has the purpose of eliminating a by-product which can form during the bioconversion, namely triolphosphate which corresponds to the alcohol non yet oxidized to acid, which is esterified in the form of a phosphate (formula (IIIb)) described below.

On the other hand this process lends itself to industrial use. By operating with a concentration of starting product of 0.5 g/l, the yield exceeds 70% relative to the starting product.

Among the other advantages of the use of the microbiological route against the chemical route, the non polluting aspect of this technique can be emphasized, all the operations taking place in aqueous media.

The purification is carried out according to the methods known to a person skilled in the art. It can be purification by crystallization, by chromatography or by ion exchange resin.

The salification reactions can be carried out under the usual conditions. For example the operation can be carried out in the presence of ethanolic soda. A sodium salt can also be used such as sodium or potassium carbonate or acid carbonate. The salts obtained can be the salts of alkali or alkaline-earth metals or optionally substituted ammonium.

The implementation of the oxidation is carried out according to the methods which are currently used for the microbiological oxidation of organic molecules using cultures of filamentous fungi (Holland H L, Organic synthesis with oxidative enzymes. VCH publisher, Inc, New York 1992; Lacroix I, Biton J and Azerad R, Microbial biotransformation of a synthetic immunomodulating agent HR325, Bioorg. Med. Chem. (1997) 7, 1369–1380; Sebek O K, Fungal transformations as a useful method for the organic synthesis of organic compounds, Mycologia 75(2) 383–394, 1983; Azerad, R. Microbial models for drug metabolism, Advances in Biochemical Engineering and Biotechnology, Vol. 63, page 169, 1999.

Thus, firstly, the most favourable fermentation conditions are determined by analytical route, in particular by thin layer chromatography or HPLC, in prior tests, such as for example the choice of the nutrient medium, the solvent of the appropriate substrate, the concentration of substrate, the technical conditions such as temperature, aeration, pH, and the optimum periods for the culture, addition of the substrate and contact of the substrate with the microorganism.

In a first phase, the culture is carried out from an inoculum (spores or mycelium) of *Absidia corymbifera* LCP 63-1800 or a bacteria of the *Streptomyces* genus, in particular *Streptomyces platensis* NRRL 2364, in a liquid nutrient medium at an initial pH of 5 to 7 and at a temperature of 20 to 30° C., preferably from 26 to 28° C. Aeration is ensured by rotary agitation of the culture receptacles (150 to 250 rpm) or, in the fermentation vessel, by the introduction of air at a flow rate of approximately 1 l/min and per liter of broth culture medium.

After a time varying from 24 to 72 hours, preferably 60 to 65 hours, the terfenadine is added at a concentration of 0.1 to 1 g/liter, preferably 0.4 to 0.6 g/liter, in solution in an organic solvent which is miscible with water, such as ethanol, acetone, tetrahydrofuran, dimethylformamide or dimethylsulphoxide (5 to 20 ml/liter of culture), preferably ethanol (10 ml/liter). The incubation is continued under the same conditions as the culture. The pH is optionally readjusted and maintained at a value of 5.0 to 8.0. The conversion of the substrate is advantageously followed by HPLC analysis of the incubation supernatant or thin layer chromatography of samples extracted with an organic solvent. In general after 48 to 200 hours, sufficient quantities of Fexofenadine have been formed.

Another procedure consists of separating the biomass of the culture medium by filtration, washing it with water or a solution buffered to a neutral pH, then resuspending it in a suitable buffer, for example a 0.05 M phosphate buffer at pH 7, then adding the substrate and continuing the incubation as described previously.

The isolation and purification of the products of the process is carried out in a manner which is known per se. For example, the products of the process can be extracted with an organic solvent, preferably ethyl acetate, or by adsorption on a hydrophobic column, followed by elution with an organic solvent, evaporating the organic solvent, separating and purifying the products by column chromatography or by crystallization.

Therefore a more particular subject of the invention is the process as described previously in which the biotransformation conditions are as follows: concentration of terfenadine added from 0.5 g/l to 10 g/l and preferably from 0.5 g/l to 5 g/l, pH evolving between 5.0 and 8.0, temperature comprised between 26° C. and 28° C. and aeration by the introduction of an air flow of approximately 1 l/min. and per liter of culture broth medium.

One of the objectives of the invention is to adjust the pH during the incubation and optionally to maintain it at an optimized value, with a view to minimizing the formation of by-products.

Conversion of the Terfenadine (II) to Fexofenadine (I) by *A. corymbifera* or *S. platensis* involves several successive stages, with the intermediate formation of the triol (IIIc) and that of two undesired by-products, Terfenadine-phosphate (IIIa) and triolphosphate (IIIb) according to the diagram below:

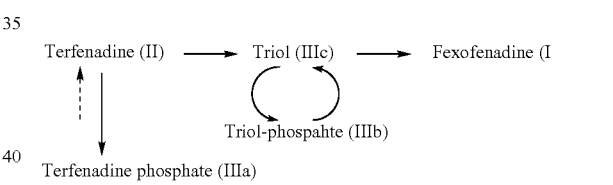

(IIIa)

Terfenadine-P

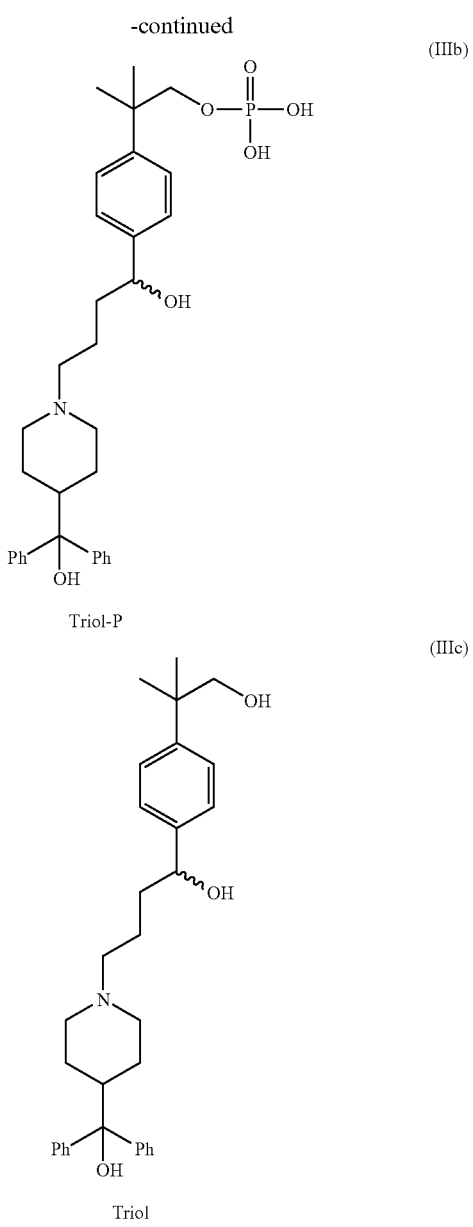

Triol-P

Triol

The initial oxidation of terfenadine (I) to triol (IIIc), produced by the microorganism in the incubation medium, is encouraged by a slightly acid or neutral pH (6<pH<7) (Table 2). The formation (apparently irreversible) of Terfenadine-phosphate (IIIa) remains very limited in all the conditions studied and less than 1–2%. On the other hand, the formation of triol-phosphate (IIIb) represents a significant part of the oxidation products accumulated in the medium, particularly when the incubation is carried out at a neutral or alkaline pH (pH 7.0–8.0) as shown in Table 3 (see also FIG. 1); this is the pH towards which the incubation medium naturally evolves. However, at a slightly more acid pH (optimum pH ~6), a phosphatase of fungal origin, present in the incubation medium, catalyzes the rapid hydrolysis of the triol-phosphate (IIIb) (Table 4, FIG. 1), whilst the irreversible oxidation of the triol to fexofenadine is encouraged at a higher pH (pH >7) (Table 5, FIG. 1).

As a result there are several possible strategies for transforming almost all of the Terfenadine to Fexofenadine (if one does not take into account the very small quantity of Terfenadine-phosphate formed):

firstly proceeding with incubation in the initial culture medium at a pH of approximately 6.5, without monitoring the pH, which leads (at the same time as the pH evolves towards 8.0–8.5) to a complete transformation of the terfenadine to a stable stationary mixture of triol-phosphate (IIIb) and fexofenadine (FIG. 2) (Examples 2 and 3), then lowering the pH to a value comprised between 3.5 and 4 in order to encourage the transformation of (IIIb) to (IIIc) and allowing it to slowly and spontaneously rise towards 6.0, until the complete disappearance of the triol-phosphate (IIIb), then readjusting and maintaining the pH in the region of 8.0, until transformation of the triol (IIIc) to fexofenadine (FIG. 3) (Example 4).

proceeding in the same manner with an incubation in the culture medium, initially at a pH of approximately 6.5, without monitoring the pH, (the pH naturally evolves towards 8.0–8.5) then lowering and maintaining it at a value comprised between 6.0 and 6.5, at which pH the triol-phosphate (IIIb) is quite rapidly hydrolyzed, as a result of the equilibrium of phosphatase-phosphorylase activities at this pH, whilst the triol (IIIc) is itself quite rapidly oxidized, until virtually complete transformation to fexofenadine (FIG. 4) (Example 5).

A more particular subject of the invention is therefore:

a process as defined above in which the initial pH at approximately 6.5,
  naturally evolves to 8.0–8.5, which leads to a mixture of triol-phosphate (IIIb) and a compound of formula (I),
  is then lowered to a value comprised between 3.5 and 4 in order to encourage the transformation of the intermediate compound of formula (IIIb) to the intermediate compound of formula (IIIc),
  then naturally evolves to approximately 6.0 until the complete disappearance of compound (IIIb),
  and finally is readjusted and maintained at approximately 8.0 until transformation of compound (IIIc) to Fexofenadine.

a process as defined above in which the initial pH is approximately 6.5
  naturally evolves to 8.0–8.5,
  is then lowered and maintained at a value comprised between 6.3 and 6.8.

a process as defined above in which during the purification stage, extraction of the product of formula (I) is carried out in the ethyl acetate.

Finally, a subject of the invention is also, as intermediate compound, the compound of formula (IIIc), as defined above.

The following examples illustrate the invention without however limiting it.

Preparation of the Different Culture Media

Medium A: Corn steep liqueur, 10 ml; NaNO$_3$, 2 g; MgSO$_4$.7H$_2$O, 0.5 g; FeSO$_4$.7H$_2$O, 0.02 g; KCl, 0.5 g for 900 ml of distilled water. Phosphate buffer (K$_2$HPO$_4$, 2 g; KH$_2$PO$_4$, 1 g in 40 ml of distilled water) and glucose, 30 g in 60 ml of distilled water, added at the moment of seeding.

Medium B: Soya peptone, 5 g; yeast extract, 5 g; MgSO$_4$7H$_2$O, 0.5 g; NaNO$_3$, 2 g; KCl, 0.5 g; FeSO$_4$.7H$_2$O, 0.02 g for 900 ml of distilled water. Phosphate buffer (K$_2$HPO$_4$, 2 g; KH$_2$PO$_4$, 1 g in 40 ml of distilled water) and glucose, 30 g in 60 ml of distilled water, added at the moment of seeding.

Medium C: Soya peptone, 5 g; yeast extract, 5 g; NaCl, 5 g; $K_2HPO_4$, 5 g for 900 ml of distilled water. Glucose, 100 ml of a solution at 200 g/L added at the moment of seeding.

Medium D: Corn steep liquor, 10 ml; soya peptone, 5 g; $NaNO_3$, 2 g; $MgSO_4.7H_2O$, 0.5 g; $FeSO_4.7H_2O$, 0.02 g; KCl, 0.5 g for 900 ml of distilled water. Phosphate buffer ($K_2HPO_4$, 2 g; $KH_2PO_4$, 1 g in 40 ml of distilled water) and glucose, 30 g in 60 ml of distilled water, added at the moment of seeding.

Medium E: Medium C adjusted to pH 7 with concentrated HCl, before sterilization.

EXAMPLE 1

Study of the Different Microorganisms (Screening)

For the screening, 250 ml Erlenmeyer flasks containing 100 ml of culture medium are seeded with a suspension of spores freshly harvested on solid medium and growth is carried out in a rotary incubator at 27° C. and 200 RPM for 66 hours.

The Terfenadine is added in solution in ethanol (10 ml/liter) at a final concentration of 0.2 g/l directly to the biomass in its culture medium.

Incubation is continued under the same conditions as the culture for 7 days.

a) Analytical Methods

Regular samples (1 ml per day) of the supernatant are taken during the incubation, centrifuged, microfiltered and injected into HPLC on a column of nucleosil C18 (250×4 mm; flow rate: 1 ml/min; detection at 220 nm and at 60° C.; the solvent is an acetonitrile-water-trifluoroacetic acid (TFA) gradient constituted from the $CH_3CN$-water-TFA (100:900:1) (solvent A) and $CH_3CN$-water-TFA (900:100:1) (solvent B) mixture.

Under these conditions, terfenadine (II) has a retention time of 14.56 min., terfenadine-P (IIIa), a retention time of 11.8 min., triol (IIIc), a retention time of 9.61 min., fexofenadine, a retention time of 9.45 min. and triol-P (IIIb), a retention time of 7.43 min.

b) Results of the Screening

The realisation of a screening under the culture conditions described above produces, among other strains tested, the results noted in the table below and allowed 2 strains *Absidia corymbifera* LCP 63-1800 and *Streptomyces platensis* NRRL 2364 to be found, which are capable of producing fexofenadine in an Erlenmeyer flask with a good yield, but in the presence of a non negligible quantity of triol phosphate and triol.

TABLE 1

Metabolization of terfenadine by various microorganisms, 0.2 g/l, 96 hours, 27° C.

|  | Terfenadine (a) | Triol-p | Fexafenadine | Triol | Terfenadine-p |
|---|---|---|---|---|---|
| *Absidia blakesleeana* ATCC 6811 | + | − | − | − | − |
| *Absidia blakesleeana* ATCC 42838 | − | ± | − | − | − |
| *Absidia blakesleeana* ATCC 22617 | − | − | − | − | − |
| *Absidia blakesleeana* ATCC 10148b | − | ± | − | − | − |
| *Absidia blakesleeana* ATCC 22739 | − | ± | − | − | − |
| *Absidia corymbifera* LCP 63.1800 | − | ± | +++ | + | − |
| *Absidia corymbifera* LCP 64.1942 | − | − | ± | − | − |
| *Absidia corymbifera* LCP 86.3480 | − | ± | ± | − | − |
| *Actinomucor elegans* MMP 2092 | ± | + | ± | − | − |
| *Aspergillus ochraceus* ATCC 1008 | − | − | ± | − | − |
| *Cunninghamella blakesleeana* ATCC 8688a | ± | ± | − | ± | ± |
| *Cunninghamella echinulata* LCP 73.2203 | ± | − | − | ± | − |
| *Cunninghamella echinulata* NRRL 3655 | ± | ± | − | ± | ± |
| *Cunninghamella elegans* ATCC 9245 | ± | − | − | − | + |
| *Streptomyces platensis* NRRL 2364 | − | − | + | +++ | − |

(a): Only the culture supernatants were tested, which explains the absence of terfenadine adsorbed on the mycelium.
±: 5–10% (HPLC)
+: 10–20% (HPLC)
+++: 70–80% (HPLC)

c) Purification and Complete Characterization of the Fexofenadine formed by *Absidia cozymbifera* LCP 63.1800

Starting with an Erlenmeyer flask of *Absidia corymbifera* (100 ml-20 mg of terfenadine), after filtration of the mycelium and washing with water, the supernatant is saturated with NaCl then extracted 3 times with ethyl acetate; the organic phase is dried over $MgSO_4$ then evaporated under reduced pressure in order to produce 27 mg of a whitish solid residue which is purified by chromatography on a silica gel column (230–400 mesh) using the solvent: $CH_2Cl_2$—MeOH—$NH_4OH$ (82.5: 15: 2.5). 12.4 mg of pure product is recovered identical to authentic fexofenadine. M.p.=190–195° C.

d) Structural Study of the Fexofenadine Obtained Using *Absidia corymbifera* LCP 63-1800

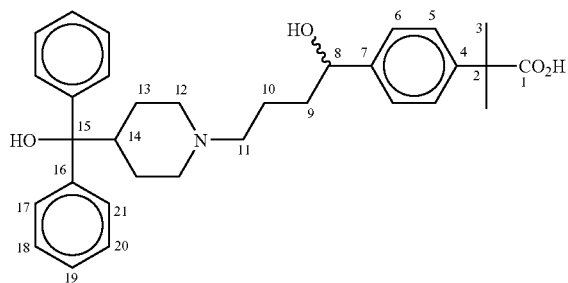

NMR $^1H$ ($CD_3OD$, 250.13 MHz) Δ, ppm: 1.49 (6H, s, 2 $CH_3$), 1.55–1.82 (8H, m, H-9, H-10 and H-13), 2.73–2.85 (4H, m, H-12), 3.30–3.32 (2H, m, H-11), 4.60 (1H, dd, J=5.57 and 5.97 Hz, H-8), 7.17 (2H, d, J=7.17 Hz, H-5), 7.29 (6H, dd, J=7.17 and 7.97 Hz, H-18, H-19 and H-20), 7.39 (2H, d, J=8.37 Hz, H-6), 7.53 (4H, d, J=7.57 Hz, H-17 and H-21).

NMR $^{13}C$ ($CD_3OD$, 62.9 MHz) Δ, ppm: 23.7 ($CH_2$, C-10), 27.1 (2 $CH_2$, C-13), 30.2 (2 $CH_3$, C-3), 39.0 ($CH_2$, C-9), 44.9 (CH, C-14), 50.9 (quat. C, C-2), 55.4 (2 $CH_2$, C-12), 59.5 ($CH_2$, C-11), 75.5 (CH, C-8), 81.7 (quat. C, C-15), 23.7 ($CH_2$, C-10), 128.6; 123.9; 129.4 and 131.0 (CH, C-5, C-6, C-17, C-18, C-19, C-20 and C-21), 145.2; 149.2 and 150.3 (quat. C, C-4, C-7 and C-16), 186.3 (quat. C, C-1).

MS (electrospray, negative ions), m/z: 500 ($M-H^+$), 456 ($M-H^+$—$CO_2$), 378 (456-$C_6H_6$)

EXAMPLE 2

Microbiological Preparation of Fexofenadine

Ten 250 ml Erlenmeyer flasks containing 100 ml of medium D are seeded with *A. corymbifera* LCP 63-1800. 50 mg of Terfenadine in 1 ml of ethanol is added to each Erlenmeyer flask. On D+7, the 10 Erlenmeyer flasks are filtered on gauze (the supernatant has a pH equal to 8.0), and saturation with sodium chloride is carried out for 2 hours (pH=5–6), followed by extracting 3 times with ethyl acetate and drying over magnesium sulphate. After evaporation under reduced pressure, 409 mg of expected crude product is obtained (yield=77%, approximately 90% pure product).

This product is purified on a column of silica gel (230–400 mesh, 40 g of silica, diameter 3 cm) eluting with a methylene chloride/methanol/ammonium hydroxide mixture (82.5–15–2.5). 312 mg of pure fexofenadine is recovered (61.4%)

EXAMPLE 3

Preparation of Fexofenadine in a Fermentation Vessel (Medium A)

The culture of *Absidia corymbifera* is carried out in medium A (pH 6.5), but in a Biolafitte fermentation vessel, in a volume of 5 liters inoculated with $2.10^6$ spores/liter, at 27° C., with a flow rate of air of approximately 5 liters/min. and stirring (helicoidal impeller) of 275 revs/min. The biomass obtained after culture for 66 hours and which is in the form of homogeneous pellets approximately 1 mm in diameter was used for the bioconversion directly in the culture fermentation vessel. 1.25 g of Terfenadine in 50 ml of ethanol are added and incubation is continued under the same conditions for 7 days. At this stage, the pH is 8.5 and the incubation medium contains 35% of fexofenadine and 65% of triolphosphate. The biomass is separated from the liquid medium by filtration. The filtrate is saturated with NaCl, its pH is adjusted to 6.0 with dilute HCl and it is extracted 3 times with ethyl acetate. After purification as described in Example 2, 350 mg (27%) of pure fexofenadine is recovered. The triolphosphate (IIIb) in the aqueous phase can be recovered by adsorption on a column of XAD-2 and elution with methanol.

EXAMPLE 3a

Preparation of Fexofenadine in a Fermentation Vessel (medium D)

The culture of *Absidia corymbifera* is carried out in medium D (pH 6.5), in a Biolafitte fermentation vessel, under the same conditions as in Example 3. The biomass obtained after culture for 66 hours is used for the bioconversion directly in the culture fermentation vessel. 1 g of Terfenadine in 25 ml of ethanol are added and the incubation is continued under the same conditions for 4 days. At this stage, the pH is 8.0 and the incubation medium contains 70% of fexofenadine and 30% of triolphosphate which are isolated and purified as described in Example 3.

EXAMPLE 4

Method with Successive Adjustments of the pH for the Preparation of Fexofenadine in a Fermentation Vessel The culture of *Absidia corymbifera* is carried out in medium D (pH 6.5), under the conditions described in Example 3. 2.5 g of Terfenadine in 50 ml of ethanol are added and the incubation is continued under the same conditions for 4 days. At this stage, the pH is 8.0 and the incubation medium contains 42% of fexofenadine, 13% of triol (IIIc) and 25% of triolphosphate (IIIb). The pH is adjusted to 3.5 with concentrated HCl and the incubation is continued under the same conditions leaving the pH of the medium to evolve freely up to 6 (3 days). At this stage, the triol-phosphate (IIIb) has virtually totally disappeared in favour of the triol. The pH is readjusted to 8.0 and the incubation is continued under the same conditions for another 2 days. The medium then contains 85% of fexofenadine and 13% of triol phosphate (IIIb).

EXAMPLE 5

Optimized Method for the Preparation of Fexofenadine in a Fermentation Vessel The culture of *Absidia corymbifera* is carried out in medium D (pH 6.5), under the conditions described in Example 3. 2.5 g of Terfenadine in 50 ml of ethanol is added and the incubation is continued under the same conditions for 4 days. At this stage, the pH is 8.0 and the incubation medium contains 35% of fexofenadine, 11.5% of triol (IIIc) and 34% of triolphosphate (IIIb). The pH is adjusted and maintained at 6.0–6.5 with dilute HCl whilst the incubation is continued under the same conditions (3 days). The medium then contains 89.5% of fexofenadine and 9.5% of triol phosphate.

EXAMPLE 6

A 250 ml Erlenmeyer flask containing 100 ml of medium E is seeded with *Streptomyces platensis* NRRL 2364 and cultured as described in Example 1. Half of the culture medium and the biomass, the pH of which is 5.0, has 10 mg of terfenadine dissolved in 0.5 ml of ethanol added to it and incubation is continued for several days under the same conditions. After 3 days, the only metabolite observed is the triol (IIIc) (60 %); after 7 days the triol yield reaches 67%.

EXAMPLE 7

The other half of the culture medium and the biomass of Example 6, has terfenadine (10 mg in 0.5 ml of ethanol) added to it and incubated under the same conditions as in Example 6 for 3 days, then taken to pH 8.0 by adding 7.5 M NaOH. The incubation is continued for another 4 days and 16% of triol-phosphate (IIIb), 37% of fexofenadine (I) and 26% of triol (IIIc) are obtained.

EXAMPLE 8

Preparation of Fexofenadine in a Fermentation Vessel

Preculture

The preculture is carried out in minimum medium (the carbon source is glucose) in 500 ml Erlenmeyer flasks containing 100 ml of sterile medium. The Erlenmeyer flasks are seeded with 450 µl of a glycerolized suspension of *Streptomyces platensis* NRRL 2364 (stock frozen at −80° C.) and incubated in an orbital shaker (2.5 cm orbit size) at 34° C., 250 rpm for 75 hours.

Fermentation/Bioconversion

The fermentation is carried out in fermentation vessels with a total volume of 500 ml containing 300 ml of minimum medium at 125 g/l of glucose. The fermentation vessel is inoculated with 7.5 ml of the preculture described above. The culture conditions are as follows:

Temperature adjusted to 34° C.

Constant stirring (no regulation of pO2)

Constant aeration at 54 l/h (3vvm)

PH adjusted to 6.0 by the addition of KOH at 20% At 48 hours of culture, 75 mg of terfenadine solubilized in 3 ml of ethanol is added. Culture is continued until 212 hours have passed.

Results

For this test, the terfenadine and its derivatives are assayed by reversed-phase HPLC after dilution of the culture broth media to 1/10 in ethanol. At 212 hours 71% advancement of the reaction is obtained (fexofenadine formed) and a balance estimated at 82%.

TABLE 2

Initial rate of oxidation of the Terfenadine as a function of the pH (Biomass after 66 hours, washed and resuspended in a 0.05 M phosphate buffer in the presence of terfenadine 1061 µmol/litre). The measurement carried out by HPLC corresponds to the sum (triol + triol-phosphate + fexofenadine)

| pH | Oxidized Terfenadine (total) µmol/l/h |
|---|---|
| 6.3 | 1.60 |
| 6.5 | 2.45 |
| 7.0 | 0.60 |
| 7.5 | 0.59 |
| 8.0 | 0.76 |

TABLE 3

Initial rate (after 2 hours of incubation) of phosphorylation of the triol as a function of the pH (Biomass after 66 hours, washed and resuspended in a 0.05 M phosphate buffer in the presence of triol 186 µmol/litre). The triol-phosphate formed in the incubation supernatant are measured by HPLC (no formation of fexofenadine was observed in the first 2 hours)

| pH | Triol-phosphate µmol/l/h |
|---|---|
| 6.3 | 53.5 |
| 6.5 | 57.0 |
| 7.0 | 41.5 |
| 7.5 | 27.0 |
| 8.0 | 24.0 |

TABLE 4

Initial rate of hydrolysis of the triol-phosphate as a function of the pH (incubation supernatant after 120 hours containing 272 µmol/litre of triol-phosphate, adjusted and maintained at different pHs by concentrated HCl and incubated at 27° C.). The hydrolysis is measured by HPLC both by the disappearance of triol-phosphate and the appearance of triol. The initial rate is calculated on the average of the samples carried out for the first 7.5 hours of hydrolysis.

| pH | After 4 hours of incubation | | After 24 hours of incubation | | Initial rate of hydrolysis of the triol-phosphate µmol/l/h |
|---|---|---|---|---|---|
| | residual triol-phosphate µmol/l (% hydrolysis) | triol produced µmol/l (% hydrolysis) | residual triol-phosphate µmol/l (% hydrolysis) | triol produced µmol/l (% hydrolysis) | |
| 4.0 | 258 (5%) | 12 (4.4%) | 223 (18%) | 35 (13%) | 3.13 |
| 5.0 | 234 (14%) | 40 (14.7%) | 148 (45.6%) | 120 (44.1%) | 8.71 |
| 6.0 | 196 (27.9%) | 68 (25%) | 50 (81.7%) | 216 (79.4%) | 17.49 |
| 6.5 | 224 (17.6%) | 30 (11%) | 140 (48.5%) | 131 (48.2%) | 8.71 |
| 7.0 | 237 (12.9%) | 30 (11%) | 167 (38.6%) | 109 (40%) | 7.12 |
| 7.5 | 240 (12%) | 31 (11.4%) | 181 (33%) | 77 (28.3%) | 5.48 |
| 8.0 | 244 (10%) | 19 (7%) | 197 (28%) | 69 (25.4%) | 4.37 |

TABLE 5 oxidization of the triol measured between 6 hours and 24 hours of incubation as a function of the pH (Biomass after 66 hours, washed and resuspended in a 0.05 M phosphate buffer in the presence of triol 186 μmol/litre). During this time interval where the fexofenadine is formed, the concentration of triol is stationary. The two products are measured by HPLC.

| pH | Triol at the time 6–24 hours μmol/litre | Triol-phosphate at the time 6–24 hours μmol/litre | Fexofenadine produced between 6 and 24 hours μmol/litre (%)* |
|---|---|---|---|
| 6.3 | 110–130 | 65–27 | 0 (0) |
| 6.5 | 93–96 | 72–31 | 15 (15.6) |
| 7.0 | 46–58 | 110–64 | 25 (45.1) |
| 7.5 | 21–43 | 124–61 | 30 (69.7) |
| 8.0 | 20–49 | 128–41 | 30 (61.2) |

*% calculated = (fexofenadine formed/residual triol) × 100

FIG. 1: Summary of the influence of the pH on the four unitary reactions of the metabolism of terfenadine by *A. blakesleeana*. The scale of the ordinates was recalculated by multiplication for each curve to values of the same order.

Figure 2:
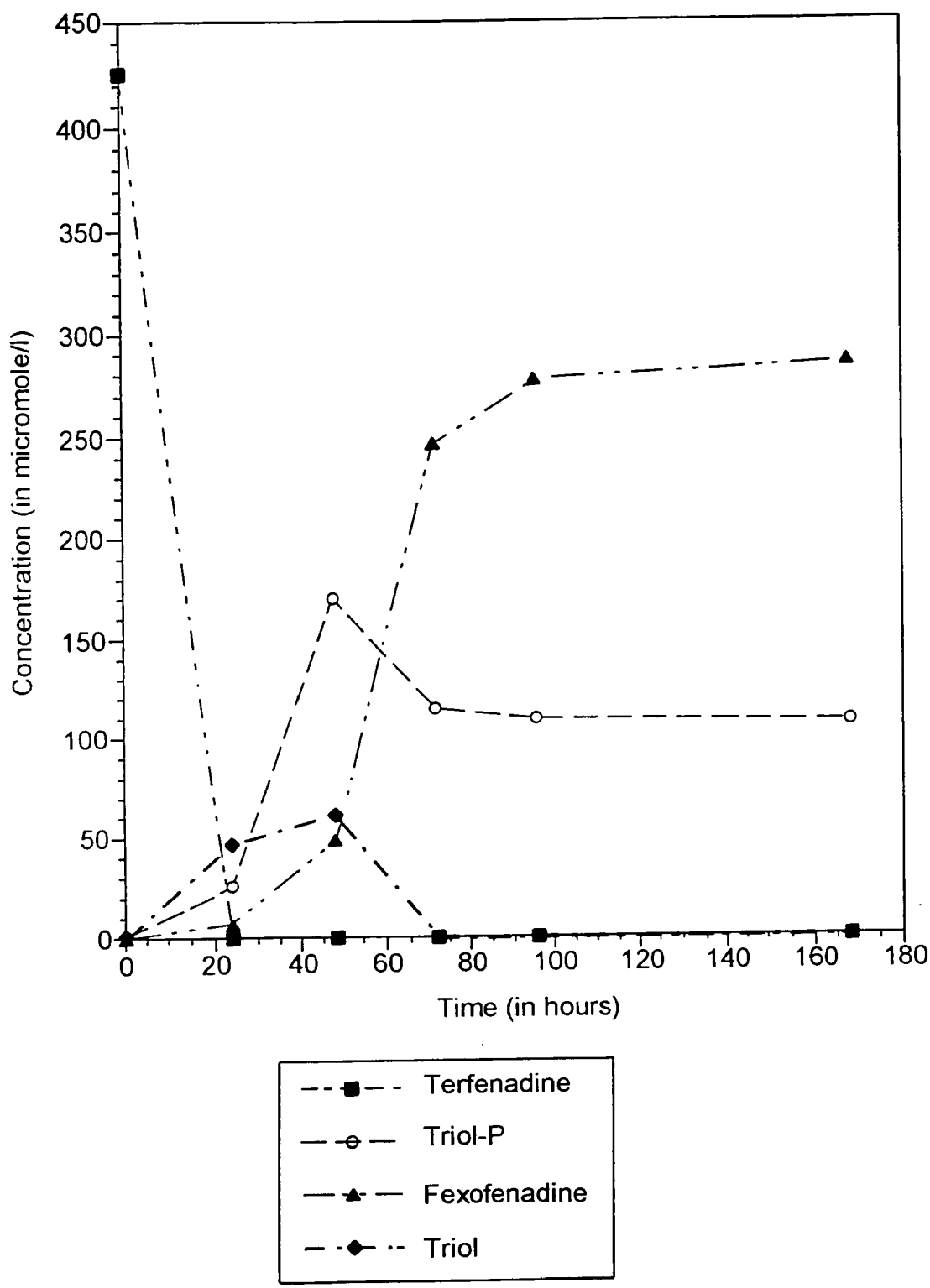

FIG. 2: Bioconversion of terfenadine (0.2 g/l) in medium D, without monitoring of pH.

Figure 3:
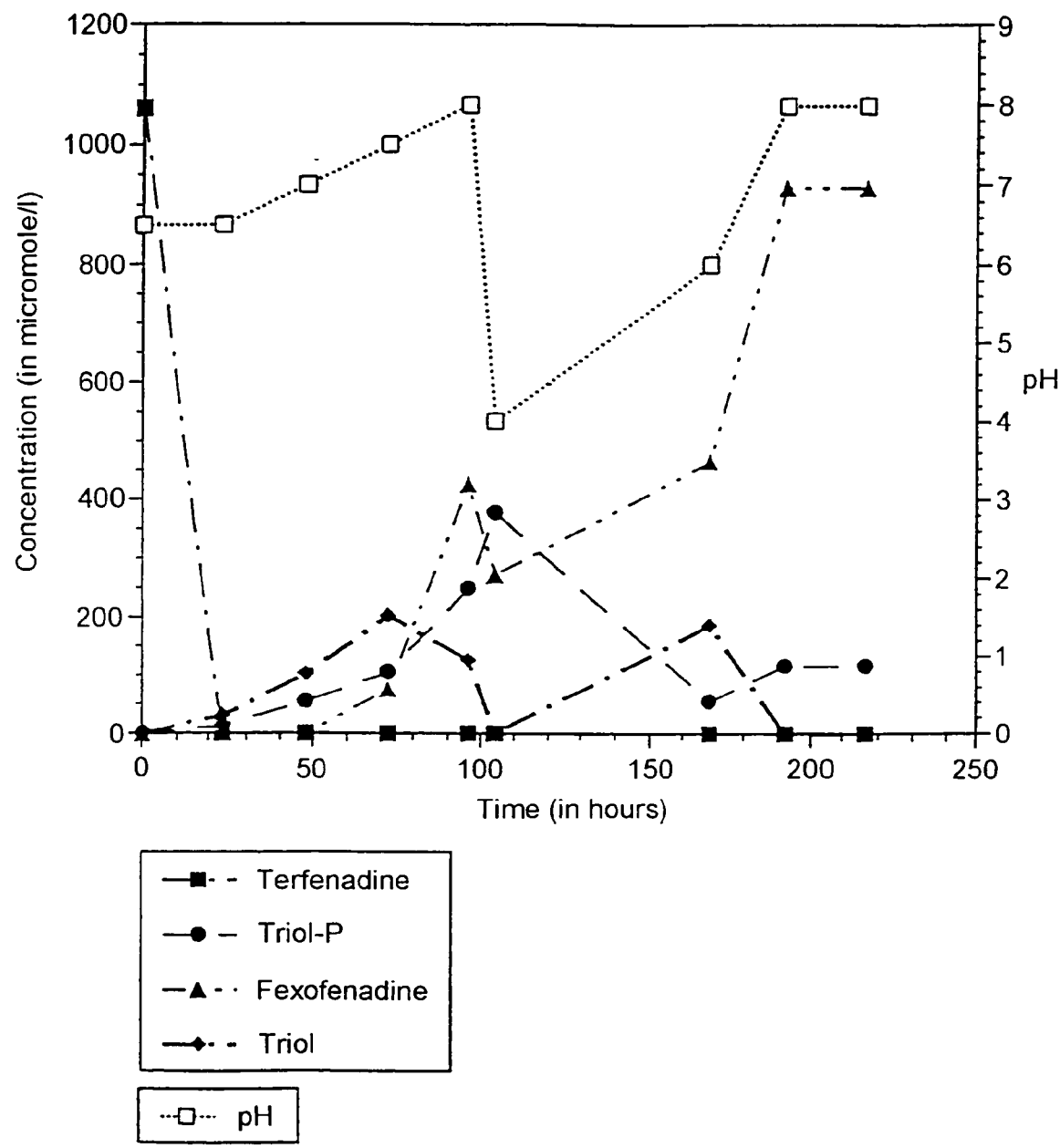

FIG. 3: Bioconversion of terfenadine (0.5 g/l) in a 100 ml Erlenmeyer flask in medium D with adjustment of the pH of the incubation to 3.5 (96 hours) and 8.0 (168 hours).

Figure 4:
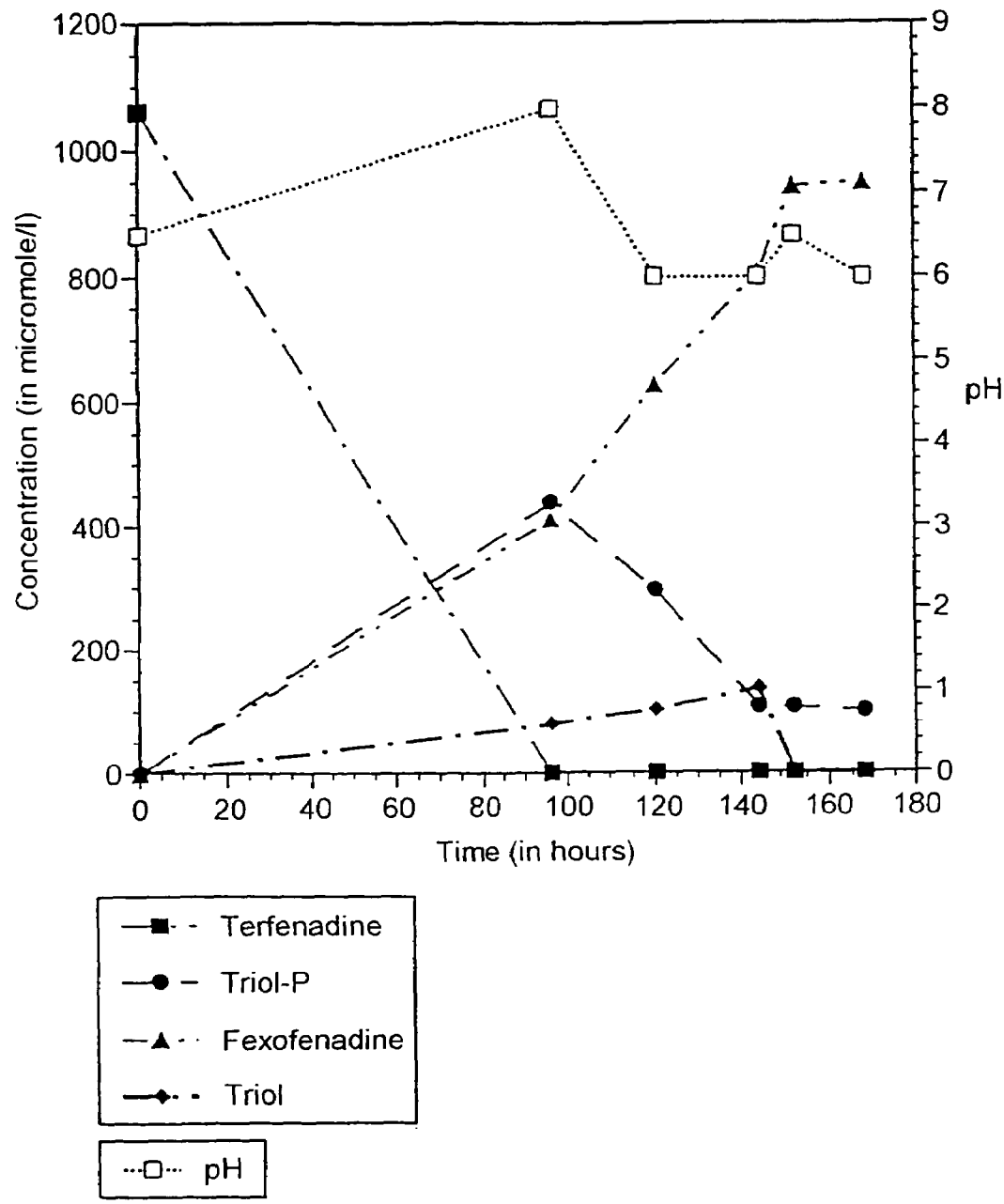

FIG. 4: Bioconversion of terfenadine (0.5 g/l 27° C., medium D) in an Erlenmeyer flask by *A. blakesleeana* with modification and maintenance of the pH of the incubation at 6.0 after 96 hours.

What is claimed is:

1. A process for preparing a compound of formula I

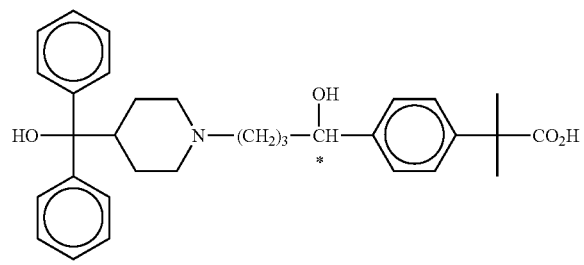

(I)

comprising subjecting a compound of formula II

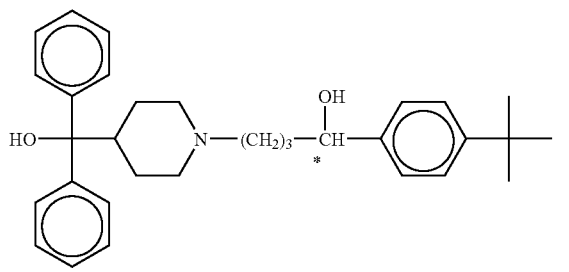

(II)

to bioconversion with a microorganism culture of *Absidia corymbifera* LCP 63-1800 at a pH of 5.0 to 8.0 to obtain the compound of formula I, and optionally isolating, purifying or salifying the compound of formula I, wherein the compounds of formulate I and II are in an enantiomeric forms or a mixture of the enantiomeric forms thereof.

2. The process according to claim 1 wherein the compound of formula II is a racemic mixture of its enantiomers resulting in a racemic mixture of the enantiomers of formula I.

3. The process according to claim 1 wherein the bioconversion is effected at concentration of 0.5 to 10 gram per liter of the compound of formula II at a temperature of 26 to 28° C. with aeration with an airflow of about 1 liter/minute and per liter of culture broth medium.

4. The process according to claim 1 wherein the pH initially is about 6.5 and naturally evolves to 8.0 to 8.5 to obtain a mixture of triolphosphate of the formula

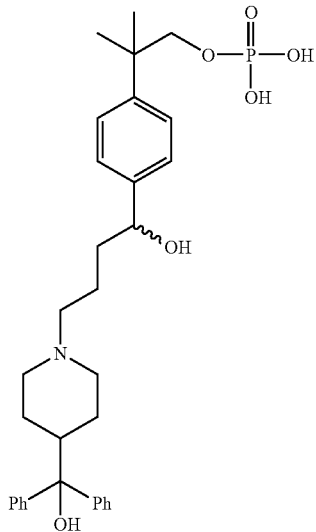

III$_b$ and the compound of formula I, the pH of the mixture is reduced to a value of 3.5 and 5 to convert the compound of Formula IIIb into an intermediate compound of formula III$_c$

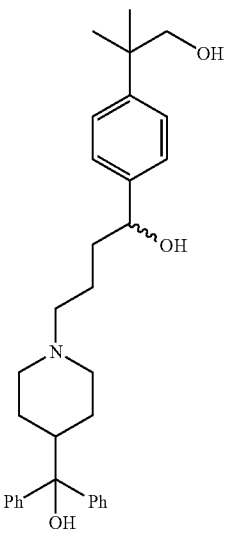

III$_c$

Triol wherein the pH evolves naturally to a value of 6.0 until the compound of formula III$_b$ is completely dispensed, and the pH is adjusted to about 8 to obtain the compound of Formula I.

5. The process according to claim 1 wherein the pH initially is about 6.5, naturally evolves to 8.0 to 8.5, and then is reduced and maintained at 6.3 to 6.8.

6. The process according to claim 1 wherein the compound of formula I is purified by extraction with ethylacetate.

* * * * *